(12) United States Patent
Daniel et al.

(10) Patent No.: US 11,207,185 B2
(45) Date of Patent: *Dec. 28, 2021

(54) SPLITTING ATTACHMENT FOR GRAFT CONTAINMENT CAGE

(71) Applicant: DePuy Synthes Products, Inc., Raynham, MA (US)

(72) Inventors: Steffan Daniel, Zuchwil (CH); André Furrer, Zuchwil (CH); Simon Bosshard, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 544 days.

This patent is subject to a terminal disclaimer.

(21) Appl. No.: 15/409,026

(22) Filed: Jan. 18, 2017

(65) Prior Publication Data

US 2017/0216033 A1 Aug. 3, 2017

Related U.S. Application Data

(60) Provisional application No. 62/288,257, filed on Jan. 28, 2016.

(51) Int. Cl.
*A61F 2/28* (2006.01)
*A61F 2/30* (2006.01)
*A61F 2/46* (2006.01)

(52) U.S. Cl.
CPC .......... *A61F 2/2846* (2013.01); *A61F 2/2803* (2013.01); *A61F 2/4644* (2013.01); *A61F 2002/2835* (2013.01); *A61F 2002/3092* (2013.01); *A61F 2002/30535* (2013.01); *A61F 2002/30578* (2013.01); *A61F 2002/30784* (2013.01); *A61F 2002/30909* (2013.01); *A61F 2002/30914* (2013.01);

(Continued)

(58) Field of Classification Search
CPC .................. A61F 2/2846; A61F 2/2803; A61F 2002/30909; A61F 2002/30915; A61F 2002/3092; A61F 2002/30914; A61F 2002/2835

See application file for complete search history.

(56) References Cited

U.S. PATENT DOCUMENTS

| | | | |
|---|---|---|---|
| 4,903,691 A | 2/1990 | Heinl | |
| 8,197,520 B2 * | 6/2012 | Salemi | A61B 17/8085 606/280 |

(Continued)

FOREIGN PATENT DOCUMENTS

| | | |
|---|---|---|
| CN | 101394810 | 3/2009 |
| CN | 102940522 | 2/2013 |

(Continued)

*Primary Examiner* — Marcia L Watkins
(74) *Attorney, Agent, or Firm* — Fay Kaplun & Marcin, LLP

(57) ABSTRACT

A bone graft containment device includes a body extending longitudinally from a first end to a second end. The body is defined via a strut framework sized and shaped to correspond to an outer surface of a target bone. The strut framework defines an interior space configured to receive a bone graft or bone graft substitute material. The device also includes a first grasping structure and a second grasping structure extending from an exterior of the body. The first and second grasping structures are configured to receive a bone fixation plate therebetween.

22 Claims, 2 Drawing Sheets

(52) U.S. Cl.
CPC ............... *A61F 2002/30915* (2013.01); *A61F 2220/0008* (2013.01); *A61F 2310/00359* (2013.01)

(56) References Cited

U.S. PATENT DOCUMENTS

| | | | | |
|---|---|---|---|---|
| 8,840,614 | B2 * | 9/2014 | Mikhail | ................. A61F 2/2803 606/86 R |
| 9,011,540 | B1 * | 4/2015 | Castro | ....................... A61F 2/44 606/280 |
| 9,925,046 | B2 * | 3/2018 | Larsen | ................. A61F 2/2846 |
| 2005/0273165 | A1 | 12/2005 | Griffiths et al. | |
| 2008/0021476 | A1 * | 1/2008 | Kirschman | ........ A61B 17/7059 606/288 |
| 2008/0172095 | A1 | 7/2008 | Salerni et al. | |
| 2010/0161061 | A1 | 6/2010 | Hunt | |
| 2011/0313532 | A1 | 12/2011 | Hunt | |
| 2012/0053587 | A1 * | 3/2012 | Kiritsis | .................. A61B 17/17 606/71 |
| 2013/0164707 | A1 | 6/2013 | Ali | |
| 2017/0216034 | A1 * | 8/2017 | Daniel | ................. A61F 2/2803 |
| 2018/0193530 | A1 | 7/2018 | Barbas et al. | |

FOREIGN PATENT DOCUMENTS

| | | |
|---|---|---|
| CN | 203017072 | 6/2013 |
| CN | 103298429 | 9/2013 |
| CN | 103 445 883 | 12/2013 |
| CN | 103536347 | 1/2014 |
| DE | 36 01 715 | 7/1987 |
| DE | 9115341 | 2/1992 |
| EP | 2 550 922 | 1/2013 |
| JP | 2015507491 | 3/2015 |
| WO | 9216170 | 10/1992 |
| WO | 0059409 | 10/2000 |
| WO | 2012/068062 | 5/2012 |
| WO | 2013/006778 | 1/2013 |
| WO | 2015/138657 | 9/2015 |

* cited by examiner

SPLITTING ATTACHMENT FOR GRAFT CONTAINMENT CAGE

PRIORITY CLAIM

The present application is a Non-Provisional Application which claims priority to U.S. Provisional Patent Application Ser. No. 62/288,257 filed on Jan. 28, 2016. The specification of the above-identified application is expressly incorporated herein by reference.

BACKGROUND

Mandible defects are often treated with bone grafts and/or implants such as, bone plates, to assist with healing. The bone grafts may be placed in the target area using any of a variety of methods. However, without a container for the bone graft, the graft may fall away from a target site before it can be incorporated by the body into the healing bone.

SUMMARY

The present invention is directed to a bone graft containment device, comprising a body extending longitudinally from a first end to a second end, the body defined via a strut framework sized and shaped to correspond to an outer surface of a target bone, the strut framework defining an interior space configured to receive a bone graft or bone graft substitute material and a first grasping structure and a second grasping structure extending from an exterior of the body, the first and second grasping structures configured to receive a bone fixation plate therebetween.

The present invention is also directed to a bone graft system, comprising a graft containment device including a body extending longitudinally from a first end to a second end and sized and shaped to correspond to an outer surface of a target bone, the body defined via a strut framework having an interior space configured to receive a bone graft material therein, a first grasping structure and a second grasping structure extending from an exterior of the body and a fixation plate sized and shaped to be received between the first and second grasping structures, the fixation plate extending longitudinally from a first end to a second end and including a plurality of bone fixation element receiving holes extending therethrough.

BRIEF DESCRIPTION

DETAILED DESCRIPTION

Figure 1:
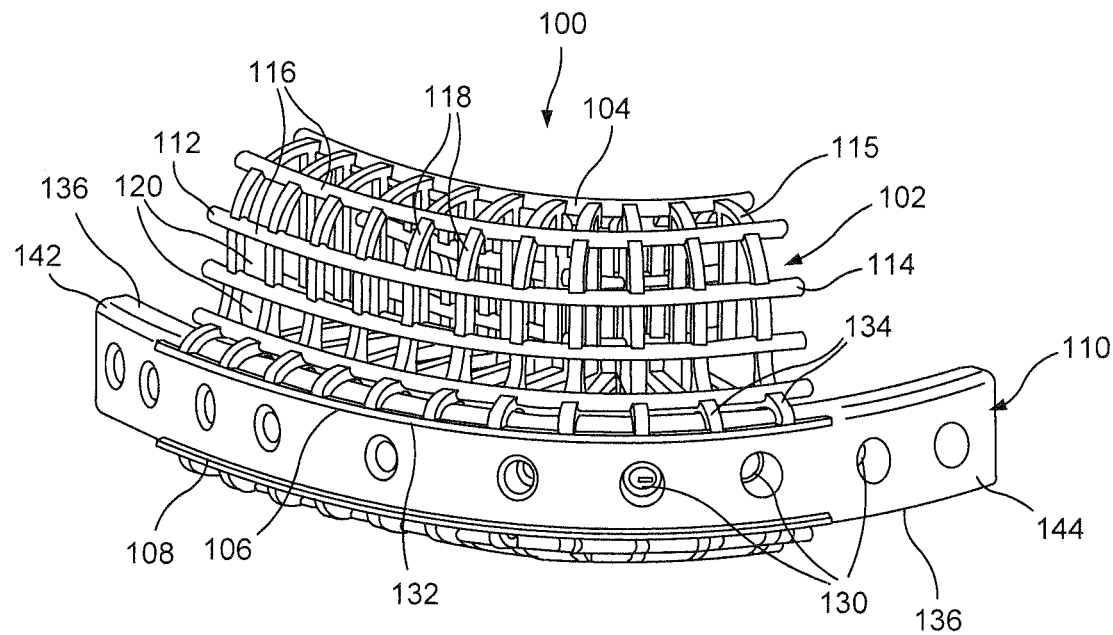
FIG. 1 shows a perspective view of a system according to an exemplary embodiment of the present invention.

The present invention may be understood with reference to the following description and the appended drawings, wherein like elements are referred to with the same reference numerals. The present invention relates to the treatment of bone and, in particular, relates to treatments using bone grafts. Exemplary embodiments of the present invention describe a graft containment cage configured to be positioned in a gap or space in a target bone (e.g., the mandible) so that graft material may be packed therein to encourage and guide the generation of new bone in the gap/space. In one exemplary embodiment, the cage may be positioned between two separated portions of bone to generate new bone joining the separated portions of bone. It will be understood by those of skill in the art, however, that the graft containment cage may be inserted or positioned within any gap or space of the target bone including, for example, at an end of the bone, so that there is bone only on one side of the graft containment cage, or within a recessed space of the bone, so that three sides of the graft containment cage contact bone. The graft containment device of the exemplary embodiment is formed as a mesh defining openings through which the bone graft material packed inside the mesh may be vascularized and incorporated into the surrounding portions of bone as desired. The graft containment device may be utilized in conjunction with an attachment such as, for example, a fixation plate for aligning separated portions of bone. In another example, the graft containment device may be utilized with an attachment including a condylar head prosthesis. In particular, the graft containment device includes an attachment grasping feature which receives and holds a fixation plate, or other attachment, so that the fixation plate may be fixed relative to the graft containment device, e.g., to stabilize the separated portions of bone during the growth of the new connecting portion of bone. The graft containment device of one embodiment is sized, shaped and structured to treat defects of the mandible. Although the exemplary embodiment is shown and described as being used in treating a mandible, it will be understood by those of skill in the art that the graft containment device of the present invention may also be formed in different shapes and sizes to permit its use in treating other types of bone which would benefit from the use of a graft containment device along with a fixation plate or other attachment.

Figure 2:
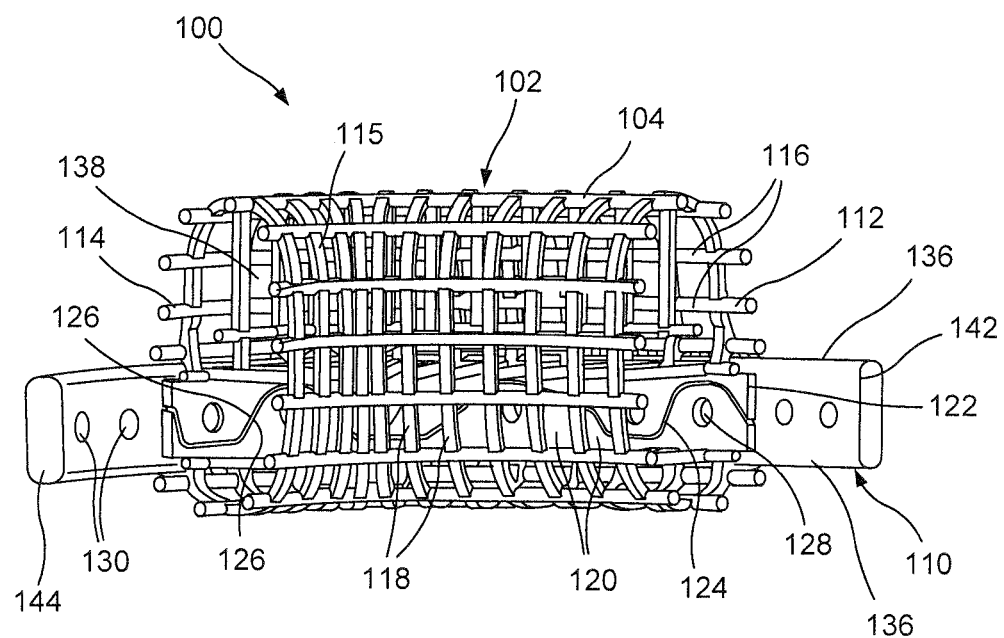
FIG. 2 shows another perspective view of the system of FIG. 1.
Figure 3:
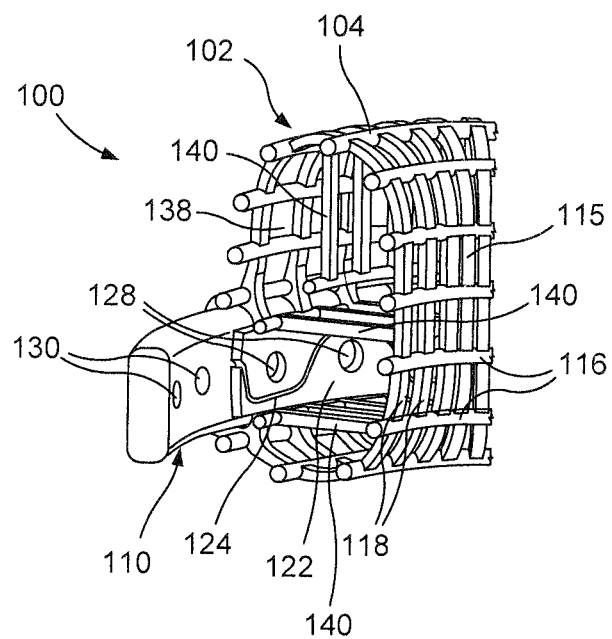
FIG. 3 shows a perspective view of a portion of the system of FIG. 1.

As shown in FIGS. 1-3, a system 100 according to an exemplary embodiment comprises a graft containment device 102 including a body 104 with first and second grasping structures 106, 108 extending therefrom sized and shaped to receive a bone fixation plate 110 therebetween. The body 104 of the graft containment device 102 is sized and shaped so that, when the graft containment device 102 is positioned in a target area between separated portions of a target bone, each of the ends of the body 104 substantially matches a profile of an outer surface of a corresponding one of the ends of the separated portions of bone. The fixation plate 110 is received between the first and second grasping structures 106, 108 so that, once the graft containment device 102 has been positioned in the target area, the fixation plate 110 may be fixed to the graft containment device 102 and to the separated portions of bone, to form a bridge maintaining the separated portions of bone in a target alignment. The graft containment device 102 may be formed via a strut framework 115 so that the graft containment device 102 may be three dimensionally constructed (e.g., via 3D printing) to match a patient's specific bone dimensions, which may be obtained via, for example, 3D imaging of the target bone. In particular, the 3D scan data may be used to generate a desired path, size and curvature of intersecting struts while desired characteristics of the containment device 102 may be used to select a target distance between adjacent struts to generate a containment device 102 that has optimal mechanical properties while matching the patient anatomy. For example, the spacing between the struts may be selected to obtain a desired size of openings formed by the struts to ensure sufficient vascularization while securing the bone graft material within the containment device 102.

The fixation plate 110 may also be customized based on the patient's specific bone dimensions. In particular, a length and a curvature of the fixation plate 110 may be determined based on the patient specific data (e.g., 3D scan data). The fixation plate 110, however, is not required to be customized to a specific patient's bone dimensions. As would be understood by those skilled in the art, standard bone plates may be used in conjunction with a containment device 102 and modified using known techniques (e.g., bending, etc.).

The body 104 of the graft containment device 102 extends longitudinally from a first end 112 to a second end 114 and generally defines a shape corresponding to the profile of the outer surface of the target bone—particularly, the mandible. For example, a shape and size of a body 104 corresponding to a missing portion of mandible may be formed as a mirror image of a corresponding portion of the mandible on the opposite side of the jaw with end portions specifically sized and shaped to match the ends of the separated portions of the mandible which the body is to join. The body 104 is formed via a strut framework 115 comprising a plurality of first struts 116 intersecting a plurality of second struts 118. In one embodiment, the first struts 116 may extend along a length of the body 104 while the second struts 118 extend substantially perpendicular to the first struts 116. It will be understood by those of skill in the art, however, that the first and second struts 116, 118 may have any of a number of configurations so long as the first and second struts 116, 118 intersect one another to form a mesh pattern. For example, the first and second struts 116, 118 may intersect one another at a non-perpendicular angle. The first and second intersecting struts 116, 118 define openings 120 through which bone graft material may be packed into an interior space 138 defined via the strut framework 115 of the body 104. As would be understood by those skilled in the art, the openings 120 are sized to achieve a desired level of vascularization while holding the graft material within the body 104. In addition, the openings 120 may be sized to permit bone graft material to be packed into the body 104 therethrough. Furthermore, as would be understood by those skilled in the art, the size of the openings 120 may vary at different locations on the body 104 depending on factors that may influence the ease of migration out of the body 104 such as the presence or absence of tightly surrounding tissue and the position of certain openings with respect to gravity. Thus, the openings 120 may be larger in areas surrounded tightly by tissue which will aide in holding the graft material within the body 104 while being made smaller in areas without such tissue that often face downward as does the lower surface of the mandible.

The body 104 may further include a solid (non-mesh) portion 122 extending along the length of the body 104. In this embodiment, when the graft containment device 102 is positioned in a target area between two separated portions of a mandible, the solid portion 122 extends along an exterior surface (e.g. front) of the mandible. A split 124 extends along a length of the solid portion 122 from the first end 112 to the second end 114 of the body 104 so that the graft containment device 102 may be opened via the split 124. In other words, edges 126 defining the split 124 may be separated from one another so that a graft material may be packed into an interior of the body 104 by opening the graft containment device 102 via the split 124, prior to positioning of graft containment device in the target area of the mandible. In one particular embodiment, the split 124 may extend along the length of the body 104 in a wave-like (e.g., oscillating) configuration. It will be understood by those of skill in the art, however, that the split 124 may extend along the length of the body 104 in any of a number of patterns and configurations so long it permits the body 104 to be opened for packing and closed to hold the graft material therein. The first and second grasping structures 106, 108 extend from opposing sides of the solid portion 122 so that, as the edges 126 of the split 124 are brought together to close the graft containment device 102, the fixation plate 110 is grasped between the first and second grasping structures 106 108, along the solid portion 122 and the two separated portions of the mandible to align the mandible with the graft containment device 102.

The solid portion 122 of this embodiment includes holes 128 extending therethrough, the holes 128 of the of graft containment device 102 positioned to correspond to bone fixation element receiving holes 130 of the fixation plate 110 when the fixation plate 110 is in a desired position relative to the graft containment device 102. In other words, a central axis of each of the bone fixation element receiving holes 130 is axially aligned with a central axis of a corresponding one of the holes 128 of the graft containment device 102 when the fixation plate 110 is in the desired position. Thus, bone fixation elements may be inserted through the bone fixation element receiving holes 130 and the corresponding holes 128 of the graft containment device 102, to fix the fixation plate 110 relative to the graft containment device 102. In an embodiment in which the split 124 extends along the length of the body 104 in a wave-like configuration, the holes 128 may extend alternatingly through the solid portion 122 on opposing sides of the split 124. In particular, the holes 128 may be positioned within peaks and troughs of the wave-like split 124 so that, when bone fixation elements are inserted through the bone fixation element receiving holes 130 and the corresponding holes of the graft containment device 102, the graft containment device 102 is fixed and held in the closed position via the bone fixation elements. Alternatively, the fixation plate 110 may be held in place by suture or other material passed through the holes 128 and 130 as would be understood by those skilled in the art. Where the split 124 does not have a wave-like configuration with holes 128 extending through the solid portion 122 on opposing sides of the split, the graft containment device 102 may be held in the closed configuration via a suture, or other similar means.

In one embodiment, each of the first and second grasping structures 106, 108 may be formed as a longitudinal strut 132 with a plurality of curved struts 134 connecting the longitudinal strut 132 to the strut framework 115 of the body 104. Each of the curved struts 134 extends from, for example, a point of intersection between the first and second struts 116, 118. A curvature of the longitudinal strut 132 in this embodiment corresponds to a curvature of the fixation plate 110 so that, the first and second grasping structures 106, 108 extend over longitudinal edges 136 of the fixation plate 110, when the fixation plate 110 is grasped therebetween. It will be understood by those of skill in the art, however, that the first and second grasping structures 106, 108 may have any of a number of configurations so long as the fixation plate 110 may be grasped therebetween.

As shown in FIG. 3, the graft containment device 102 may also include a plurality of internal struts 140 extending laterally into the interior space 138 of the body 104. The internal struts 140 act to hold the graft material within the interior space 138 and to prevent migration of the graft material therein. In one embodiment, the internal struts 140 may extend substantially perpendicularly into the interior space 138, relative to the first and second struts 116, 118, from a point of intersection of the first and second struts 116, 118 with internal struts 140 positioned in any desired manner along the length of the body 104. For example, the internal struts 140 may be distributed throughout a length of the body 104 or only in portions thereof. As would be understood by those skilled in the art, the graft containment device 102 may include any number of internal struts 140 extending from any desired points along an interior of the strut framework 115 to achieve a desired control over migration of the graft material within the device 102.

The fixation plate 110 extends longitudinally from a first end 142 to a second end 144 and includes a plurality of bone fixation receiving holes 130 extending laterally therethrough. As discussed above, the fixation plate 110 may also be customized to a specific patient, using the patient's bone dimensions or, alternatively, may be made in one or more standard configurations that are adapted to each patient by the physician in a manner similar to the bending and shaping of known bone plates. The fixation plate 110, however, is not required to be customized and may be somewhat moldable or bendable to suit a specific patient's needs in the same manner as known bone plates. A length of the fixation plate 110 is selected to correspond to the target area to be treated. For example, a length of the plate 110 is generally selected to permit the first and second ends 142, 144 to extend to and overlap the separated portions of bone by a desired distance so that, the fixation plate 110 may be coupled to the separated portions of bone to align the separated portions of the bone and the graft containment device 102 as desired.

The strut framework 115 of the graft containment device 102 of one embodiment may be formed of a resorbable material such as, for example, polycapralactone (PCL). Thus, as the bone regenerates, the graft containment device 102 may be absorbed by the body so that eventually, only the fixation plate 110 remains. Alternatively, all or part of the device 102 may be formed of biocompatible materials used to form other implants such as bone plates.

According to an exemplary method, the graft containment device 102 of the system 100 is custom built (e.g., by 3D printing) to suit a specific patient's bone dimensions and needs. In particular, a target bone (e.g., mandible) of a patient may be imaged to obtain bone dimensions defining an exterior size and shape of a target portion of the bone to be replaced by the graft, along with a length of a portion of the bone to be treated (i.e., a distance between separated portions of the bone). These dimensions may be used to enter design and build the device 102 using, for example, CAD software in conjunction with the 3D scan data. As indicated above, the graft containment device 102 may be built and printed using a resorbable material or any suitable biocompatible material. The fixation plate 110 may be similarly printed based on dimensions of the target area of the bone. In particular, a length and curvature of the fixation plate 110 may be selected to suit the patient's specific bone dimensions and the dimensions of the target area to be treated. A location of the bone fixation element receiving holes 130 may also be selected to suit the patient's specific needs and anatomy. For example, the plate 110 can be dimensioned so that fixation element receiving holes 130 will be positioned away from damaged or weakened portions of bone. The fixation plate 110, however, is not required to be customized and may be selected from one of a plurality of available fixation plates. Once the graft containment device 102 and/or the fixation plate 110 have been built, the system 100 may be used to treat the bone, as described below.

Graft material is packed into the interior space 138 of the graft containment device 102 by opening the body 104 of the graft containment device 102 at the split 124. When a desired amount of graft material has been packed within the body 104, the graft containment device 102 is positioned within the target area between two separated portions of bone and moved to the closed position in which edges 126 of the split 124 are drawn against one another. The internal struts 140 aid in holding the graft material within the interior space 138. In some cases, it may be possible for additional graft material may be packed into the interior space 138 from the exterior of the body 104 via the openings 120. As discussed above, the openings 120 defined via the strut framework 115 may be sized and shaped to prevent the graft material from falling thereoutof.

As the graft containment device 102 is closed, the fixation plate 110 is grasped by the first and second grasping structures 106, 108. The fixation plate 110 is positioned between the first and second grasping structures 106, 108 so that positions of the bone fixation element receiving holes 130 correspond to the positions of the corresponding holes 128 extending through the solid portion 122 of the graft containment device 102. Bone fixation elements may then be inserted through any number of the bone fixation element receiving holes 130 and the corresponding holes 128 of the graft containment device 102, to fix the fixation plate 110 relative to the graft containment device 102. The assembly including the device 102 and the plate 110 is then inserted into the body to the desired position with the first and second ends 142, 144 of the fixation plate 110 extending over the separated portions of bone and the device 102 extending between these portions of bone in substantially the space to be occupied by the new bone which will be formed by the graft. Bone fixation elements are then inserted through the bone fixation element receiving holes 130 extending through portions of the fixation plate 110 extending over the separated portions of the bone to fix the fixation plate 110 and, thereby, the graft containment device 102 to these portions of bone to align the separated portions of bone along with the graft containment device 102 as desired.

Although the system 100 describes the graft containment device 102 as positioned between two separated portions of bone and as being utilized in conjunction with a fixation plate 110 that aligns two separated portions of bone, it will be understood by those of skill in the art that the graft containment device 102 may be positioned in or along any target gap or space in a target bone. For example, the graft containment device 102 may be positioned within a recessed area of bone so that the graft containment device 102 contacts the target bone along three sides of the graft containment device 102—e.g., at the first end 112, the second end 114 and along a length thereof. In another example, as will be described in further detail below with reference to a system 200, a graft containment device 202 may be positioned at an end of a target bone so that only one end of the graft containment device 202 contacts the bone. This graft containment device 202 may be utilized with an attachment 210 including, for example, a condylar head prosthesis 250.

Figure 4:
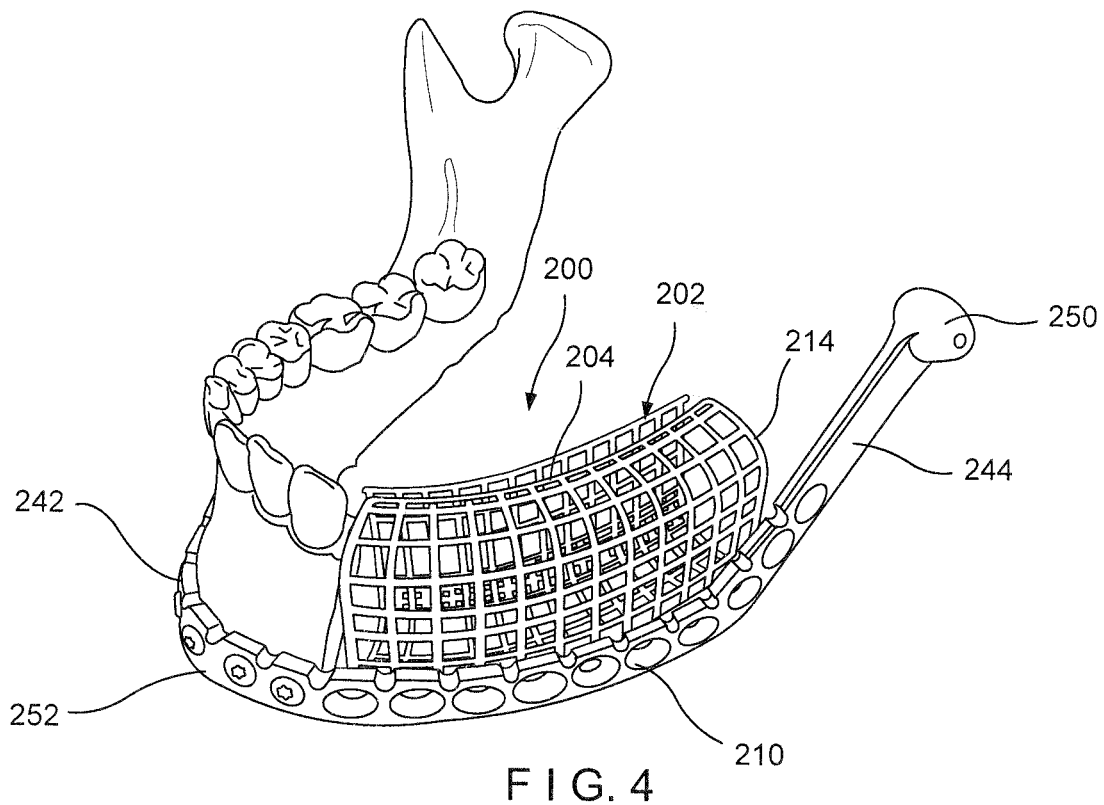
FIG. 4 shows a perspective view of a system according to another exemplary embodiment of the present invention.

As shown in FIG. 4, the system 200 according to another exemplary embodiment of the present invention comprises the graft containment device 202 and the attachment 210, which includes the condylar head prosthesis 250. The attachment 210 is configured, for example, as a fixation plate 252 including the condylar head prosthesis 250 at an end thereof. Thus, the graft containment device 202 may be used to treat a target mandible having native bone only on one side of the device 202. In aspects other than those specifically pointed out as different below, the graft containment device 202 is substantially similar to the graft containment device 102 described above with respect to the system 100. Rather than a fixation plate configured to extend across two separated portions of bone, however, the attachment 210 includes a fixation plate 252 extending from a first end 242 to a second end 244 with the condylar head prosthesis 250 extending from the second end 244 that faces the location of the condylar head to be replaced (depending on the side of the mandible (i.e., left or right) along which the system 200 is to be positioned). The system 200 is shown and described as having the condylar head prosthesis 250 at the second end 244 of the fixation plate 252 as the bone graft containment device 202 and the condylar head prosthesis 250 shown are used to treat the left side of the mandible. It will be understood by those of skill in the art, however, that the device may be formed as a mirror image with the condylar head prosthesis 250 at the first end 242 of the fixation plate 252 so that the graft containment device 202 and the attachment 210 may be similarly used to treat the right side of the mandible.

According to an exemplary method using the system 200, the graft containment device 202 is positioned along a space at an end of a mandible. For example, as shown in FIG. 4, the graft containment device 202 is positioned along a left side of a mandible as shown with the condylar head prosthesis 250 extending to the same position as the natural original condylar head. As described above with respect to the system 100, graft material is packed within the body 204 of the graft containment device 202 prior to positioning of the device 202. As would be understood by those skilled in the art after positioning the device 202 additional graft material may be added as desired. Similarly to the system 100, the fixation plate portion 252 of the attachment 210 is gripped between grasping structures of the graft containment device 202 so that the first end 242 extends over a target portion of bone (e.g., right side of the mandible) and the second end 244—which includes the condylar head prosthesis 250, extends from a second end 214 of the body 204 to be received within a temporomandibular joint of a patient's temporal bone. The attachment 210 is fixed to both the graft containment device 202 and the mandible via bone fixation elements to maintain a desired alignment between the native mandible bone and the condylar head prosthesis.

It will be understood by those of skill in the art that various modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A bone graft containment device, comprising:
   a body extending longitudinally from a first end to a second end, the body defined via a strut framework sized and shaped to correspond to an outer surface of a target bone, the strut framework defining an interior space configured to receive a bone graft material, wherein the body includes a solid portion extending along a length thereof, the solid portion including a split extending therealong, edges of the split being movable toward and away from one another to close and open the body, respectively; and
   a first grasping structure and a second grasping structure extending from an exterior of the body, the first and second grasping structures configured to extend around a portion of an exterior of a bone fixation plate and receive the bone fixation plate therebetween, the exterior of the bone fixation plate being a surface of the bone plate opposite an inner surface of the bone plate which, in a desired configuration, faces the body.

2. The device of claim 1, wherein the strut framework includes a plurality of first struts and a plurality of second struts intersecting one another.

3. The device of claim 2, wherein the plurality of first struts extend along a length of the body and the plurality of second struts extend transverse to the plurality of first struts.

4. The device of claim 1, further comprising a plurality of internal struts extending laterally from an interior of the body into the interior space.

5. The device of claim 1, wherein the split extends along the solid portion in an oscillating pattern.

6. The device of claim 1, further comprising a plurality of holes extending through the solid portion, the plurality of holes extending along a length of the solid portion on alternatingly opposing sides of the split.

7. The device of claim 6, wherein the plurality of holes extend through peaks and troughs of an oscillating pattern of the split.

8. The device of claim 1, wherein each of the first and second grasping structures comprises a longitudinal strut and a plurality of curved struts connecting the longitudinal strut to the body.

9. The device of claim 1, wherein the body is sized and shaped to be received between two separated portions of a mandible.

10. The device of claim 1, wherein the bone fixation plate and the body are separate items.

11. The device of claim 1, wherein the body and the fixation plate are configured to be joined to one another after the body has been positioned at a target location within a living body.

12. A bone graft system, comprising:
   a graft containment device including a body extending longitudinally from a first end to a second end and sized and shaped to correspond to an outer surface of a target bone, the body defined via a strut framework having an interior space configured to receive a bone graft material therein, a first grasping structure and a second grasping structure extending from an exterior of the body, wherein the body of the graft containment device includes a solid portion extending along a length thereof, the solid portion including a split extending therealong, edges of the split being movable toward and away from one another to close and open the body, respectively; and
   a fixation plate sized and shaped to be received between the first and second grasping structures, the fixation plate extending longitudinally from a first end to a second end and including a plurality of bone fixation elements receiving holes extending therethrough, the bone fixation plate including an exterior comprising a surface of the bone plate opposite an inner surface of the bone plate which, in a desired configuration, faces the body, the first and second grasping structures being configured to extend around a portion of the exterior of the bone plate.

13. The system of claim 12, wherein the strut framework includes a plurality of first struts extending along a length of the body and a plurality of second struts extending transverse to the plurality of first struts.

14. The system of claim 12, wherein the strut framework includes a plurality of internal struts extending laterally from an interior of the body into the interior space.

15. The system of claim 12, wherein the graft containment device further includes a plurality of holes extending through a solid portion.

16. The system of claim 15, wherein when the fixation plate is received between the first and second grasping structures in a desired position, each of the bone fixation elements receiving holes of the fixation plate are aligned with a corresponding one of the plurality of holes of the graft containment device.

17. The system of claim 15, wherein the plurality of holes of the graft containment device extend through peaks and troughs of an oscillating pattern of a split, alternatingly through opposing sides of the split.

18. The system of claim 12, wherein each of the first and second grasping structures comprise a longitudinal strut and a plurality of curved struts connecting the longitudinal strut to the body.

19. The system of claim 12, wherein the body is sized and shaped to be received between two separated portions of a mandible.

20. The system of claim 19, wherein a length of the fixation plate is selected so that the first and second ends thereof extend over the separated portions of the bone to align the separated portions of the mandible with the graft containment device.

21. The system of claim 12, wherein the fixation plate includes a condylar head prosthesis at one of the first end and the second end.

22. The system of claim 12, wherein the fixation plate and the body are separate items.

* * * * *